United States Patent
Larroque-Lahitette et al.

(10) Patent No.: US 9,283,002 B2
(45) Date of Patent: Mar. 15, 2016

(54) ORTHOPAEDIC DEVICE AND METHODS FOR ITS PRE-ASSEMBLY AND ASSEMBLY

(71) Applicant: Zimmer Spine, Bordeaux (FR)

(72) Inventors: Gilles Larroque-Lahitette, Lagor (FR); Georges Legallois, Bordeaux (FR); Bruno Ichelmann, Bordeaux (FR)

(73) Assignee: Zimmer Spine, Bordeaux (FR)

( * ) Notice: Subject to any disclaimer, the term of this patent is extended or adjusted under 35 U.S.C. 154(b) by 128 days.

(21) Appl. No.: 13/922,363

(22) Filed: Jun. 20, 2013

(65) Prior Publication Data

US 2013/0274808 A1    Oct. 17, 2013

Related U.S. Application Data

(63) Continuation of application No. PCT/EP2011/072806, filed on Dec. 14, 2011.

(30) Foreign Application Priority Data

Dec. 21, 2010 (EP) .................................. 10306466

(51) Int. Cl.
*A61B 17/70* (2006.01)

(52) U.S. Cl.
CPC .............. *A61B 17/705* (2013.01); *A61B 17/704* (2013.01); *A61B 17/7005* (2013.01); *A61B 17/7056* (2013.01); *Y10T 29/49963* (2015.01)

(58) Field of Classification Search
CPC ........... A61B 17/7032; A61B 17/7037; A61B 17/7049; A61B 17/705; A61B 17/7091; A61B 17/7052

USPC .................................. 606/270, 278, 250–253
See application file for complete search history.

(56) References Cited

U.S. PATENT DOCUMENTS

| | | | | |
|---|---|---|---|---|
| 5,498,262 A * | 3/1996 | Bryan | ........................... | 606/252 |
| 6,077,263 A | 6/2000 | Ameil et al. | | |
| 6,171,311 B1 * | 1/2001 | Richelsoph | ................... | 606/252 |
| 6,565,566 B1 * | 5/2003 | Wagner et al. | ................. | 606/267 |
| 6,945,972 B2 | 9/2005 | Frigg et al. | | |

(Continued)

FOREIGN PATENT DOCUMENTS

| FR | 2775583 A1 | 9/1999 |
|---|---|---|
| FR | 2775583 B1 | 8/2000 |

(Continued)

OTHER PUBLICATIONS

Written Opinion for Internationai Application No. PCT/EP2011/072806, mailed Jun. 28, 2012 8 pgs.

*Primary Examiner* — Jerry Cumberledge

(74) *Attorney, Agent, or Firm* — Schwegman Lundberg & Woessner, P.A.

(57) ABSTRACT

Orthopaedic devices including a connecting element suited for receiving at least part of a first rod, and a lock screw. The connecting element includes an anchor for securing the connecting element to a bone, in particular a vertebra, a first lateral opening, and a top opening with a first inner screw thread. The lock screw is received within the top opening and includes a proximal face presenting a screw drive, accessible from outside the connecting element, a distal end for locking the first rod within the connecting element, and wherein the lock screw is adapted to fit through the first lateral opening to be subsequently introduced into the top opening with the proximal face leading.

12 Claims, 7 Drawing Sheets

(56) References Cited

U.S. PATENT DOCUMENTS

| | | |
|---|---|---|
| 2002/0133155 A1 | 9/2002 | Ferree |
| 2004/0111088 A1 | 6/2004 | Picetti et al. |
| 2004/0260285 A1 | 12/2004 | Steib et al. |
| 2005/0154388 A1 | 7/2005 | Roussouly et al. |
| 2006/0009766 A1 | 1/2006 | Lee et al. |
| 2006/0015099 A1 | 1/2006 | Cannon et al. |
| 2006/0058787 A1* | 3/2006 | David .............................. 606/61 |
| 2006/0079892 A1 | 4/2006 | Roychowdhury et al. |
| 2006/0259038 A1* | 11/2006 | Cordaro .......................... 606/61 |
| 2007/0123860 A1* | 5/2007 | Francis et al. .................. 606/61 |
| 2007/0239159 A1 | 10/2007 | Altarac et al. |
| 2008/0058805 A1* | 3/2008 | Stuart ............................. 606/61 |
| 2008/0086126 A1 | 4/2008 | Miller |
| 2008/0177323 A1* | 7/2008 | Null et al. ..................... 606/267 |
| 2008/0243186 A1 | 10/2008 | Abdou |
| 2008/0262553 A1* | 10/2008 | Hawkins et al. ............... 606/278 |
| 2008/0294202 A1* | 11/2008 | Peterson et al. ............... 606/305 |
| 2009/0093848 A1* | 4/2009 | Neary et al. ................... 606/277 |
| 2010/0057126 A1 | 3/2010 | Hestad |
| 2010/0152785 A1* | 6/2010 | Forton et al. .................. 606/301 |
| 2010/0211114 A1* | 8/2010 | Jackson ......................... 606/302 |
| 2010/0234892 A1* | 9/2010 | Mazda et al. .................. 606/276 |
| 2013/0211467 A1* | 8/2013 | Dickinson ..................... 606/328 |

FOREIGN PATENT DOCUMENTS

| | | |
|---|---|---|
| FR | 2820968 A1 | 8/2002 |
| FR | 2849590 A1 | 7/2004 |
| WO | 9715231 A1 | 5/1997 |
| WO | 9944527 A1 | 9/1999 |
| WO | 02076315 A1 | 10/2002 |
| WO | 2010043496 A1 | 4/2010 |

* cited by examiner

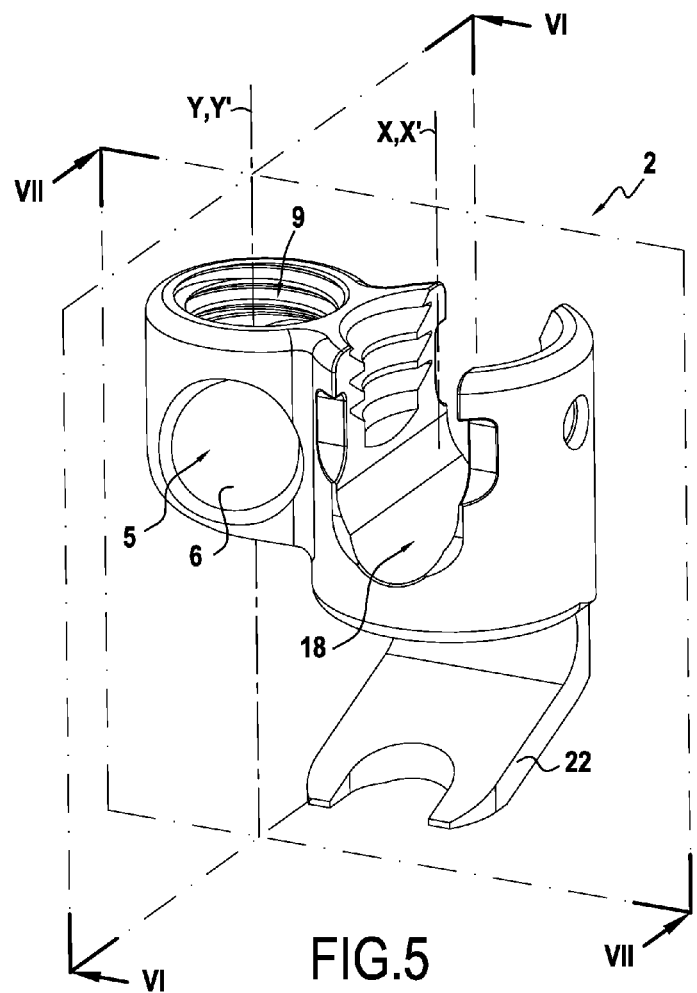
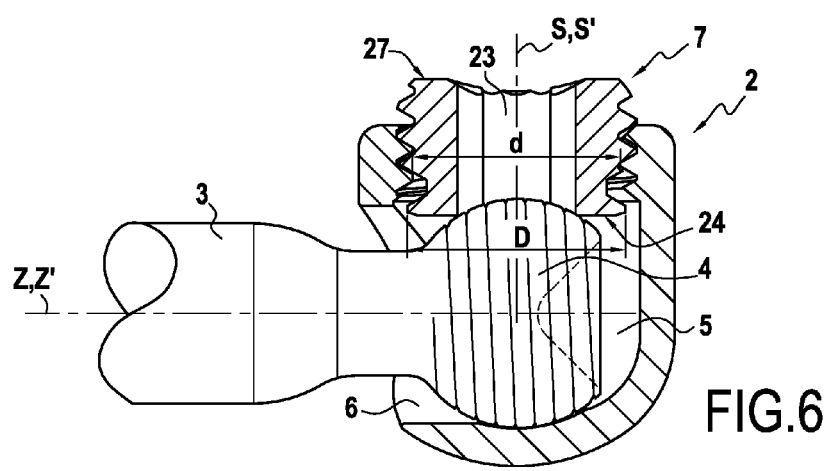
FIG.5
FIG.6

ORTHOPAEDIC DEVICE AND METHODS FOR ITS PRE-ASSEMBLY AND ASSEMBLY

CROSS-REFERENCE TO RELATED APPLICATIONS

This application is a continuation of PCT/EP2011/072806 filed on Dec. 14, 2011, which claims priority to EP10306466.3, filed on Dec. 21, 2010, the entire disclosures of which are incorporated herein by reference.

TECHNICAL FIELD

The presently disclosed systems, devices and methods relate to an orthopaedic device and in particular to an orthopaedic device suitable to be secured to a bone. One field of application for this orthopaedic device is holding bones in a relative position, for example, to aid in the healing of breaks or the positioning of bones, or the treatment of scoliosis, or otherwise to correct abnormal curvatures of the spine.

BACKGROUND

The spine is formed of superposed vertebrae, normally aligned along a vertebral axis from the lumbar vertebrae to the cervical vertebrae, each having a posterior wall from which projects a spinous process and two lateral edges from the walls of which project ribs and/or transverse process. Each vertebra also has two lateral pedicles and lamina surfaces. Accompanying FIG. 1 shows vertebrae V and V' with the different parts thereof. Reference TP designates the transversal processes, reference P designates the pedicles of the vertebra and reference L designates the lamina.

In order to straighten or stabilize the vertebrae of a spine it is well known to use a stabilizing system which includes a longitudinal connecting rod and several fixing elements. Each fixing element is secured to one of the vertebrae to be stabilized and the connecting rod is secured to each fixing element, so that portions of the connecting rod are secured to the vertebrae to be stabilized. The fixing elements include a head to be secured to the rod and a fixing member which may consist of a screw (for example a pedicle screw) or a hook. When the patient who is equipped with such a stabilizing system moves his spine, forces are developed by the fixing members of the fixing elements in the vertebrae. In particular, the fixing elements disposed at the extremities of the rod of the stabilizing system or spinal construction assembly, develop the greatest forces. It is therefore apparent that it would be advantageous to try to decrease the forces developed at the extremities of the spinal construction assembly.

For this purpose, an orthopaedic device has been previously proposed in International Patent Application WO 2010/043496 A1, comprising a first rod with a ball-shaped first end, and a connecting element. The connecting element comprises an anchor for securing said connecting element to a bone, in particular a vertebra, a socket for receiving said ball-shaped first end of the first rod so as to form a ball-and-socket joint, a first lateral opening, and a top opening with a first inner screw thread wherein a lock screw is received for locking, within said socket, said ball-shaped first end of the first rod. By "locking", in the context of the present disclosure, it is meant blocking the position of two parts with respect to each other, and only eventually also their orientation.

During the assembly of this prior art orthopaedic device, the ball-shaped first end of the first rod is introduced into the socket through the top opening of the connecting element. The lock screw can thus be threaded into the top opening only after the introduction of the ball-shaped rod end, and thus, when the connecting element is anchored to a bone, in the middle of the surgery operation, increasing the surgical staff's workload.

SUMMARY

A first object of the present disclosure is that of providing an orthopaedic device suitable for reducing the surgical staff's workload.

Accordingly, in at least one illustrative embodiment, in an orthopaedic device which comprises a connecting element suited for receiving at least part of a first rod, and a lock screw, wherein the connecting element comprises an anchor for securing said connecting element to a bone, in particular a vertebra, a first lateral opening, and a top opening with a first inner screw thread, and wherein the lock screw is received within said top opening and comprises a proximal face presenting a screw drive, accessible from outside the connecting element, and a distal end for locking said first rod within the connecting element, in order to ensure that the lock-screw, pre-assembled to the connecting element before the introduction of the first rod, said lock screw is adapted to fit through said first lateral opening to be subsequently introduced into said top opening with the proximal face leading. This would then prevent the lock screw from being even accidentally unscrewed once the ball-shaped rod end is within the socket. To further ensure that the lock screw cannot be extracted from the connecting element through the top opening, said distal end of the lock screw may be shaped so as not to fit through said top opening. The distal end may provide a thread stop, e.g. a stop collar, to enable pre-tensioning the lock screw within the connecting element. However, the extraction of the lock screw through the top opening may be prevented by alternative means, such as, for instance, a narrowed upper end of the top opening.

In order to secure the lock screw and prevent the accidental separation of lock screw and connecting element in particular by vibrations, for example during packaging, transport or other handling, in some embodiments said lock screw is pre-tensioned within the connecting element. This is achieved for instance by screwing the lock screw, within the top opening, towards a proximal direction until the screw is blocked in the thread by the thread stop.

In order to facilitate the engagement of the lock screw with the inner screw thread of the top opening of the connecting element, in at least some embodiments, the lock screw is suited to fit transversally through said lateral opening. During the pre-assembly of the lock screw, it can thus be inserted through the lateral opening already oriented in the direction of the top opening. This will subsequently facilitate screwing the lock screw upwards into the top opening.

In some embodiments, said first lateral opening has a substantially circular cross-section, providing the first rod with a substantially uniform maximum tilt angle around the ball-and-socket joint. In particular, in these embodiments, in order to better fit through said lateral opening, the proximal face of the lock screw may be convexly rounded, for instance with a single curvature cutting into the screw thread at two opposite, flattened sides of the lock screw.

In some embodiments, said connecting element further comprises a recess for receiving a second rod. In particular, the connecting element may also comprise a second inner screw thread for receiving a second lock screw for locking said second rod within said recess. The orthopaedic device thus provides a means for interconnecting an extremity of a bone support assembly, in particular a spinal support assembly, with a separate rod, said separate rod being preferably, but not necessarily, part of an autostable claw system as described in e.g. WO2010/043496.

Another object of the present disclosure is that of providing a method of pre-assembling a lock screw and a connecting element of an orthopaedic device, said connecting element comprising an anchor for securing said connecting element to a bone, in particular a vertebra, a first lateral opening, and a screw-threaded top opening.

Accordingly, in at least one embodiment of a pre-assembly method according to the invention, said lock screw engages the screw-threaded top opening before at least part of a first rod is received through said first lateral opening. The lock screw and connecting element can thus kept pre-assembled in readiness to their use, consequently reducing the workload of the surgical staff during the operation.

Advantageously, said lock screw may be introduced into said connecting element through said first lateral opening, and screwed to the screw-threaded top opening from within the connecting element. This allows the use of a lock screw with a distal end which does not fit through the top opening and thus prevents the lock screw from being extracted from the connecting element through said top opening. Once the first rod is introduced into the connecting element, limiting the movement of the lock screw in the opposite direction, the lock screw will consequently be safely secured within the connecting element.

In particular, said lock screw may be introduced transversally through said first lateral opening, so that, within the connecting element, it is directly aligned with the screw-threaded top opening, thus facilitating the pre-assembly of the lock screw with the connecting element.

Another object of the present disclosure is that of providing a method of for assembling an orthopaedic device, comprising the steps of introducing a ball-shaped first end of a first rod, through a lateral opening in a connecting element, into a socket within said connecting element so as to form a ball-and-socket joint, and tightening a lock screw against the ball-shaped first end of the first rod to lock the ball-shaped end within the socket. The connecting element further comprises an anchor for securing said connecting element to a bone, in particular a vertebra, and a screw-threaded top opening, substantially perpendicular to said first lateral opening and having said lock screw engaged therein.

Because the ball-shaped rod end is introduced into the socket through a lateral opening, the lock screw can be screwed into the top opening in advance, pre-assembling the lock screw and connecting element and reducing the workload during the assembly with the first rod.

The first rod may be introduced with the ball-shaped first end first though the first lateral opening and into the socket. However, alternatively, the ball-shaped first end may be introduced through said first lateral opening behind an opposite second end of the first rod. The first rod can thus be linked to the connecting element oriented in either direction.

Advantageously, the assembly method may also comprise the steps of receiving a second rod in a recess in said connecting element and locking said second rod within said recess, in particular by tightening a second lock screw. This has the advantage of providing a potential interconnection between an extremity of a bone support assembly, in particular a spinal support assembly, with a separate rod, said separate rod being preferably, but not necessarily, part of an autostable claw system.

The above summary of some example embodiments is not intended to describe each disclosed embodiment or every implementation thereof. In particular, selected features of any illustrative embodiment within this specification may be incorporated into an additional embodiment unless clearly stated to the contrary.

BRIEF DESCRIPTION OF THE DRAWINGS

The systems, devices and methods of the present disclosure may be more completely understood in consideration of the following detailed description of various embodiments in connection with the accompanying drawings, in which:

FIG. 5 is a perspective view of a connecting element of the orthopaedic device of FIG. 2;

FIG. 6 is a sectional view of the connecting element of FIG. 5 through plane VI-VI;

Figure 1:
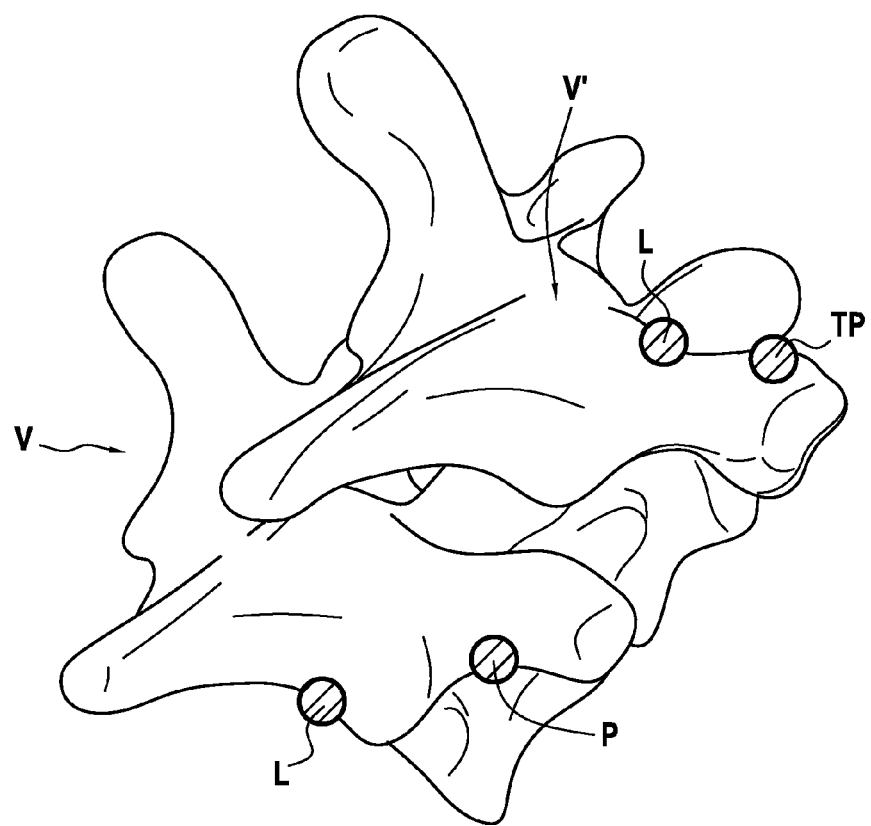
FIG. 1, already described, is a perspective view of two vertebrae showing the different parts of the vertebrae.

While these embodiments are amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the claims.

DETAILED DESCRIPTION

For the following defined terms, these definitions shall be applied, unless a different definition is given in the claims or elsewhere in this specification.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
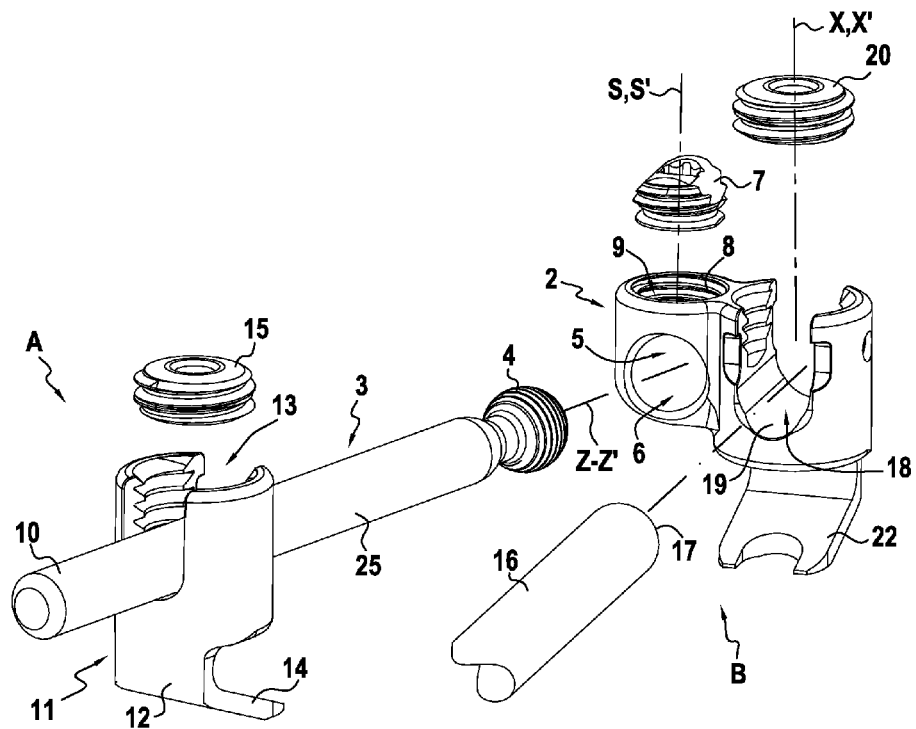
FIG. 2 is an exploded view showing an orthopaedic device according to said first embodiment of the present disclosure.
Figure 3:
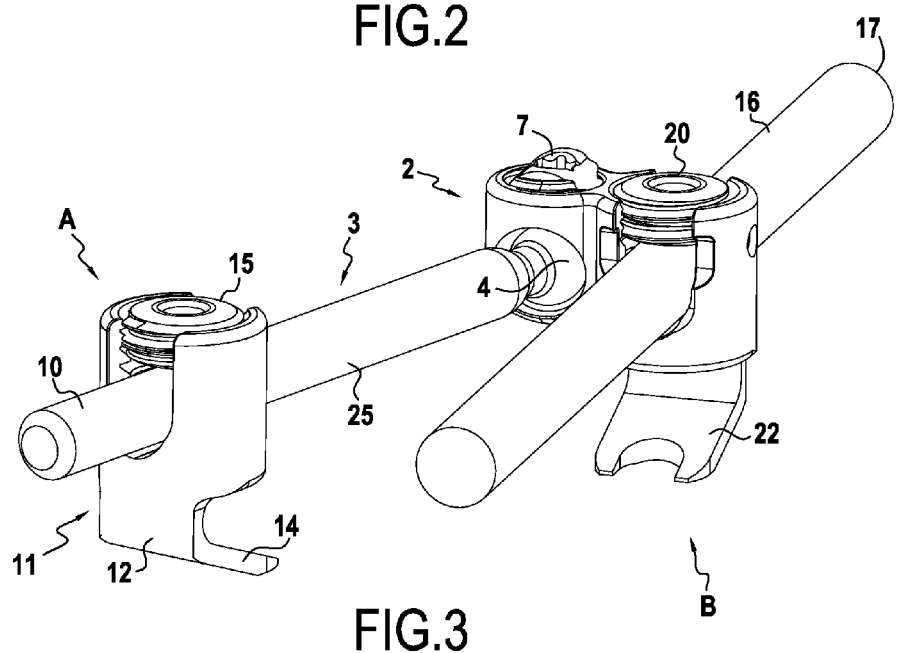
FIG. 3 is an assembled perspective view of the orthopaedic device of FIG. 2.

FIGS. 2 and 3 show an orthopaedic device 1 in the form of an autostable claw system A linked to a spinal construction assembly B over a connecting element 2. The autostable claw system A comprises a first rod 3 with a shaft 25 and a ball-shaped first end 4 forming the male part, or ball member, of a ball-and-socket joint, wherein the socket 5 of the ball-and-socket joint is defined by a partially spherical inner surface within the connecting element 2. The ball-shaped first end 4 can be introduced into the socket 5 through the lateral opening 6 and then locked within the socket 5 by means of a lock screw 7 which can cooperate with a screw thread 8 of a top opening 9 of the connecting member 2, the ball-shaped first end 4 of the first rod 3 being clamped between the lock screw 7 and the bottom of the socket 5.

The second end 10 of the first rod 3, opposite to the ball-shaped first end 4, can be connected to a fixing element 11. Preferably, the fixing element 11 comprises a connecting head 12 provided with a recess 13 to receive the first rod 3, and a hook 14 to fix the fixing element 11 to a vertebra. In the illustrated example, the hook 14 is a lamina hook, but other hook shapes and different anchor types, such as bone screws, flexible ligatures, etc., may also be considered by the skilled person.

It is therefore possible to cause the fixing element 11 to slip onto the first rod 3 (before the locking step) and the fixing element 11 may be positioned more or less close to the tip of the first rod 3. Thus, the length between the fixing element 11 and the connecting element 2 is adjustable and the device is easily implantable by the surgeon or other operative. The second end 10 of the first rod 3 can then be secured to the connecting head 12 by means of a lock screw 15.

Thanks to the ball-and-socket joint between the connecting element 2 and the first rod 3, the direction of the first rod 3 can be chosen by the surgeon, or other operative, before tightening the lock screw 7 against the ball-shaped first end 4 of the first rod 3. Thus, the surgeon can freely choose the part of the vertebra to which the fixing element 11 is fixed. This feature significantly facilitates the action of the surgeon as will be explained below with reference to FIGS. 4A to 4D.

In FIGS. 2 and 3, the spinal construction assembly B is symbolically represented by a second rod 16 having a free end 17. As is well known, the entire spinal construction assembly B can comprise, besides this second rod 16, a plurality of fixing devices (not shown in the figure) to secure intermediate portions of the second rod 16 with the vertebrae to be stabilized by the spinal construction assembly B.

The free end 17 of the rod 16 of the spinal construction assembly B is adapted to be engaged into a recess 18 of the connecting element 2. For this purpose, the diameter of a bottom wall 19 of the recess 18 is slightly greater than the diameter D of the rod 16. When the end 17 of the rod 16 is engaged into the recess 18, this end 17 is locked with respect to the connecting member by means of a lock screw 20 which cooperates with a screw thread 21, the rod 16 being clamped between the lock screw 20 and the bottom wall 19 of the recess 18.

The recess 18 may receive the second rod 16 from both sides of the connecting element 2. This facilitates the positioning of the connecting device 10 with respect to the second rod 16. In particular, it is possible to cause the connecting element 2 to slip onto the second rod 16 (before the locking step) and, thus, the connecting element 16 may be positioned more or less close to the tip of the second rod 16. The device is, therefore, easily implantable by the surgeon or other operative.

In FIGS. 2 and 3, the connecting element 2 is provided with a pedicle hook 22 with the same axis X,X' as, i.e. "aligned" with, the recess 18. However, alternative locations and orientations may be considered. For instance, it may be aligned with the socket 5. Other hook shapes and different anchor types, such as bone screws, flexible ligatures, etc., may also be considered by the skilled person. The socket 5 and the recess 18 are disposed side by side. Consequently, the connecting element 2 is less aggressive than a connecting element 2 where the two would be superposed.

FIGS. 4A to 4D illustrate the great number of possible positions of the autostable claw system A and the spinal construction assembly B. These figures also illustrate the great number of possible fixing locations of the stabilizing system to the vertebrae.

Figure 4A:
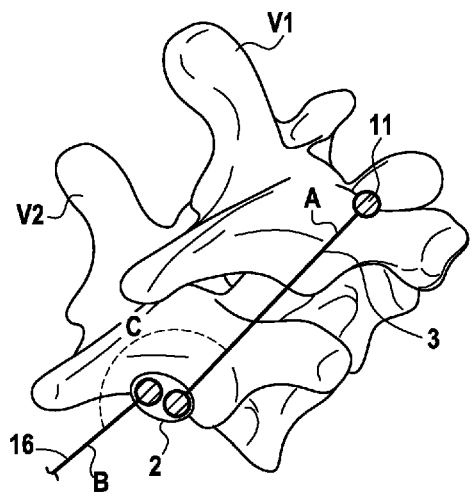
FIGS. 4A to 4D are schematic drawings which show four different combinations of a spinal construction assembly with an autostable claw system which may be achieved with the orthopaedic device of FIG. 2.

In the case of FIG. 4A, the connecting element 2 and the fixing element 11 are both fixed to a lamina of vertebrae V1 and V2, and the autostable claw system A extends beyond the spinal construction assembly B. The angle C between the rods of the systems A and B is substantially equal to 180 degrees.

Figure 4B:
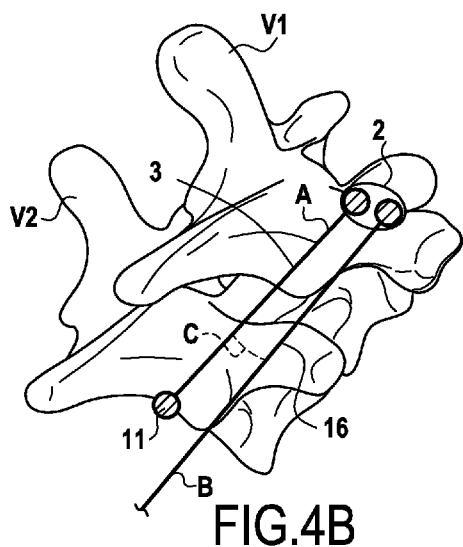

In the case of FIG. 4B, the connecting element 2 and the fixing element 11 are still secured to a lamina of vertebrae V1 and V2 but the angle C between the autostable claw system A and the spinal construction assembly B is greatly reduced. The rods of the systems A and B are substantially parallel and the assembly A "returns" towards the system B.

Figure 4C:
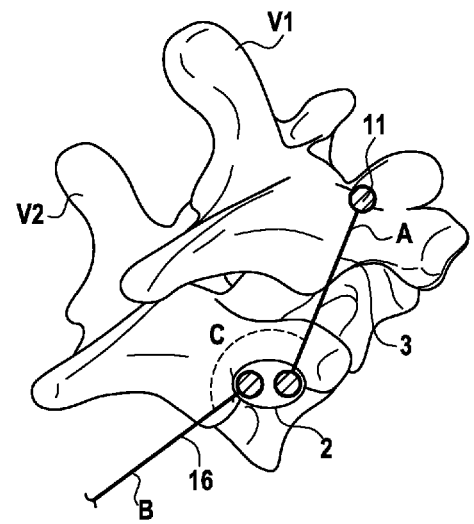

In the case of FIG. 4C, the fixing element 11 is fixed to a lamina of vertebra V1, the connecting element 2 is fixed to a pedicle of vertebra V2 and the angle C is approximately 150 degrees.

Figure 4D:
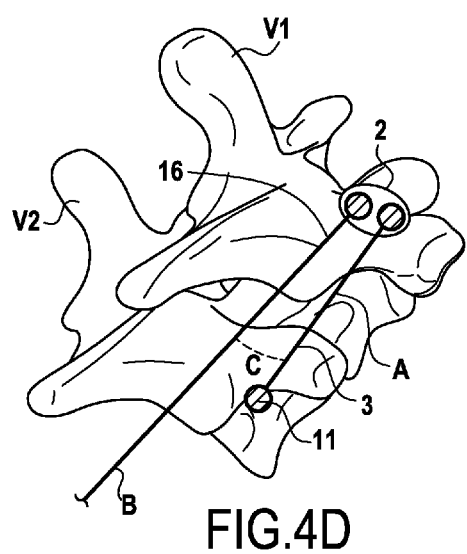

Finally, in the case of FIG. 4D, the connecting element 2 is fixed to a lamina of vertebra V1 and the fixing element 11 is secured to a pedicle of vertebra V2. The angle C is about 10 degrees. In the examples of FIGS. 4A to 4D, the fixing element 11 and the connecting element 2 are fixed to two different vertebrae. However, they may be fixed to the same vertebra.

In the illustrated embodiment, the first rod 3 is smaller in length than the second rod 16 and said first rod 3 is designed so that said connecting element 2 and said fixing element 11 are mounted on the same vertebra or on two adjacent vertebrae. The second rod 16 is designed so that more than two vertebrae are stabilized by the spinal construction assembly B. In the examples of FIGS. 4A to 4D, the first rod 3 has a straight shape and a desired length so that said connecting element 2 and said fixing element 11 are mounted on two adjacent vertebrae. In another embodiment (not shown), said connecting element 2 and said fixing element 11 may be fixed to two different parts of the same vertebra. In this case, the first rod 3 has a reduced length. In both cases, the anchoring of the extremity of the spinal construction assembly B into the vertebra is improved by the provision of the autostable claw system A.

FIG. 5 illustrates in greater detail the connecting element 2 according to the present disclosure. As discussed above, this connecting element 2 comprises a socket 5 and a recess 18 arranged side-by-side for receiving, respectively, the first rod 3 and the second rod 16. The connecting element 2 presents a lateral opening 6 and a top opening 9, both leading to the socket 5. The lateral opening 6, which is configured to receive the ball-shaped first end 4 of the first rod 3, presents a wider cross-section than the top opening 9, which has a screw thread 8 for the lock screw 7.

As can be appreciated in FIG. 6, which illustrates a section, in plane VI-VI of FIG. 5, of the connecting element 2 with the ball-shaped first end 4 of the first rod 3 within socket 5, the lateral opening 6 can accommodate the insertion of the ball-shaped first end 4 of the first rod 3 into the socket 5, as well as it extraction out of this socket 5. The lock screw 7 presents, opposite to its proximal face 27 with the screw drive 23, a broadened distal end 24 shaped so as not to fit through the screw-threaded top opening 9. For this, in this particular embodiment, the distal end 24 has a nearly round cross-section of a diameter D larger than the internal diameter d of the screw thread of the top opening 9. The lock screw 7 therefore has to be introduced into the top opening 9 from the inside of the socket 5, closing the top opening 9 before the ball-shaped first end 4 of the first rod 3 can occupy the socket 5. Moreover, when the ball-shaped first end 4 of the first rod 3 is within the socket 5, as shown in FIG. 7, the lock screw 7 cannot be removed through either opening 6 or 9.

Figure 7:
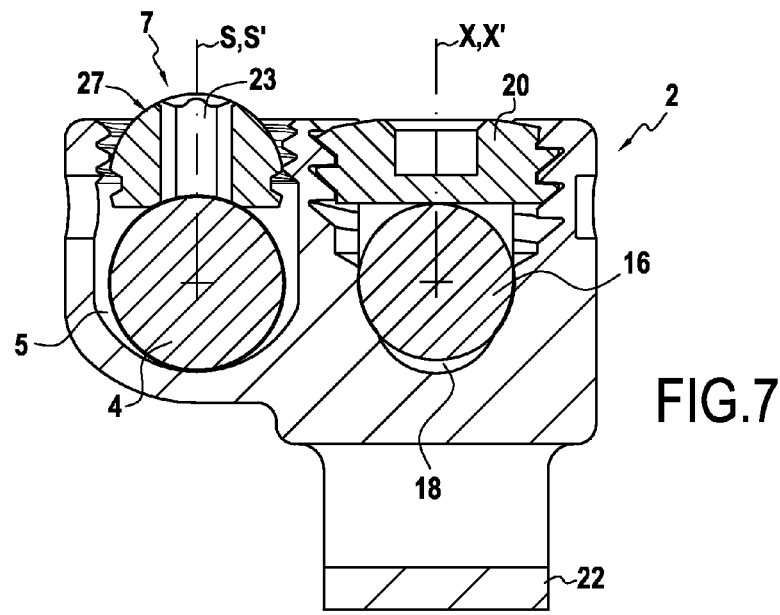
FIG. 7 is a sectional view of the connecting element of FIG. 5 through plane VII-VII.

FIG. 7 shows another, perpendicular section, in which the second rod 16, recess 18 and lock screw 20 are also visible.

Figure 8:
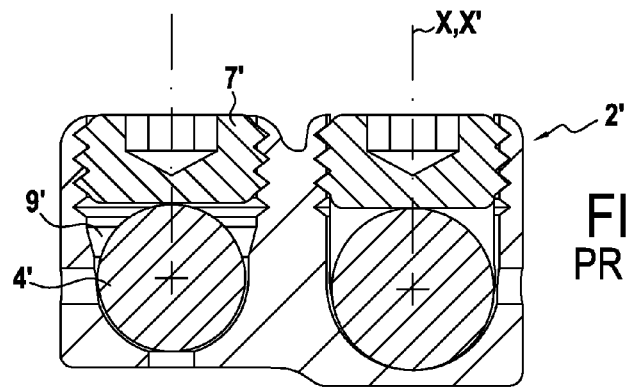
FIG. 8 is a corresponding sectional view of a prior art connecting element.

In contrast with these connecting element 2 and lock screw 7, prior art connecting element 2' and lock screw 7', as disclosed in International Patent Application Publication WO 2010/043496 A1 and illustrated in present FIG. 8, are shaped so that the ball 4' can only introduced into the socket 5' through the top opening 9', and before assembling the lock screw 7' to the connecting element 2'.

Figure 9:
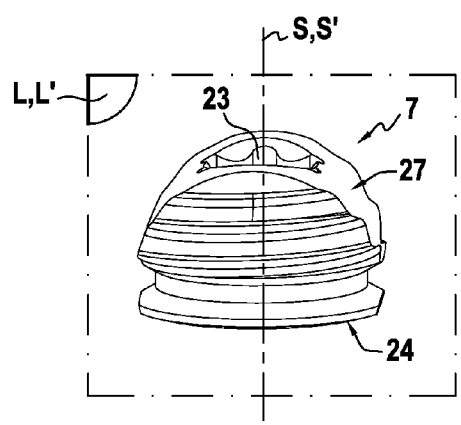
FIG. 9 is a perspective view of a lock screw for the connecting element of FIG. 5.
Figure 10:
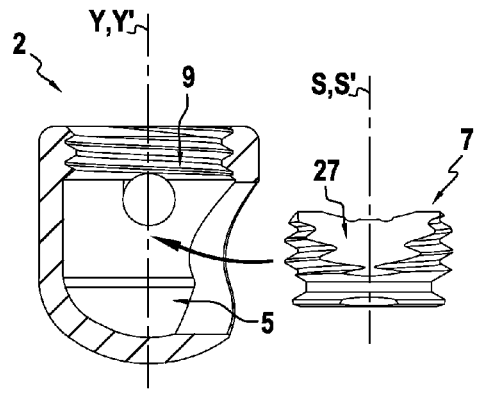
FIG. 10 shows how the lock screw of FIG. 9 is introduced in the connecting element of FIG. 5.

The lock screw 7 of the present disclosure is illustrated in greater detail in FIG. 9. The proximal face 27 presents a single curvature perpendicularly to the screw axis, cutting into the screw thread, so that this lock screw 7 presents an at least partially circular section in a longitudinal plane L-L', which is complementary to the substantially circular cross-section of the lateral opening 6 of the connecting element 2. During the pre-assembly of the lock screw 7 to the connecting element 2, the lock screw 7 can thus be introduced through the lateral opening 6 with its longitudinal axis S,S' oriented transversally to the axis Z,Z' of the lateral opening 6, as illustrated in FIG. 10. When the lock screw 7 arrives into the socket 5, its longitudinal axis S,S' comes then into alignment with the axis Y,Y' of the top opening 9 and its screw thread 8. Using its screw drive 23, the lock screw 7 can then be screwed to the top opening 9 with ease, thus pre-assembling lock screw 7 and connecting element 2. Moreover, the lock screw 7 can be pre-tensioned with a determined pre-tensioning torque as the wide distal end 24 abuts against the periphery of the top opening 9, so as to secure the lock screw 7 within the connecting element 2 against vibrations during packaging, transport and/or other manipulation.

Figure 11:
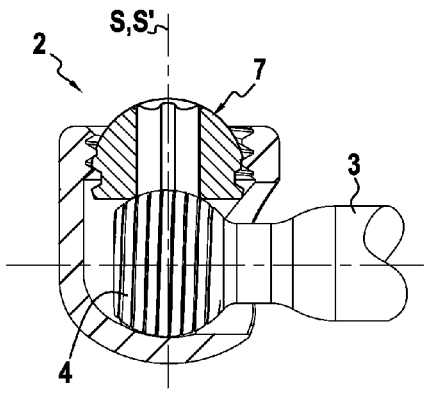
FIG. 11 shows how a ball-shaped rod end is introduced in the connecting element of FIG. 5, after the lock screw of FIG. 9.

Because the connecting element 2 and lock screw 7 according to the present disclosure can thus be easily pre-assembled even before surgery, the workload during the final assembly and implantation of the full orthopaedic device 1 is greatly facilitated, reducing the workload of the surgeon and other staff. During this final assembly, only the ball-shaped first rod end 4 of the first rod 3 is introduced into the socket 5, as illustrated in FIG. 11. Progressive tightening of the lock screw 7 against this ball-shaped first rod end 4 will first hold the ball-shaped first rod end 4 into the socket 5 while still allowing angular adjustment of the ball-and-socket joint, and then rotationally lock this ball-and-socket joint.

Figure 12:
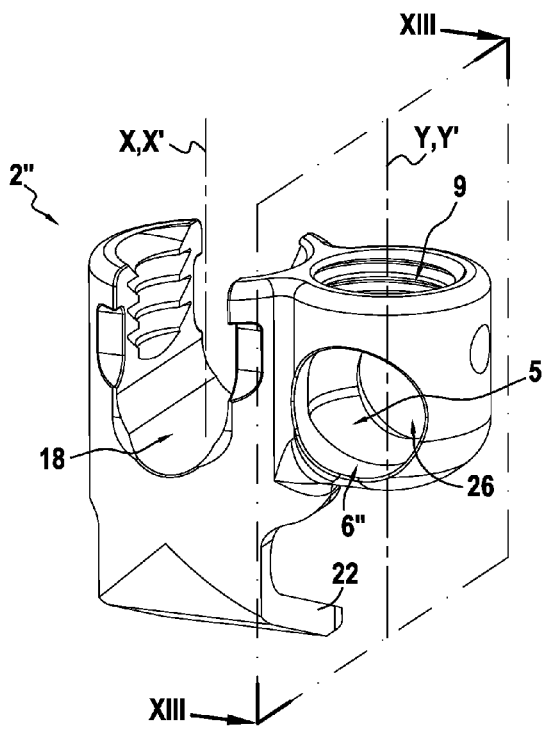
FIG. 12 is a perspective view of a connecting element of an orthopaedic device according to a second embodiment of the present invention.
Figure 13:
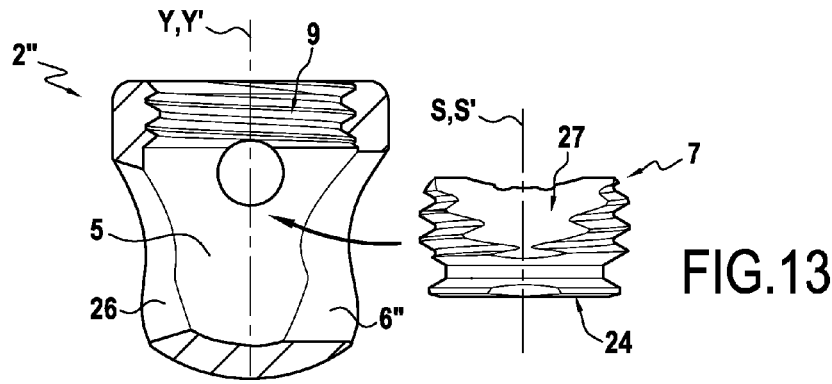
FIG. 13 is a sectional view of the connecting element of FIG. 12 through plane XII-XII.

A connecting element 2" of a second embodiment of the present disclosure is shown in FIGS. 12 and 13. This connecting element 2" comprises substantially equivalent features to those of the connecting element 2 of the first embodiment. In FIGS. 12 and 13, these substantially equivalent features accordingly receive the same references as those of the first embodiment. However, the connecting element 2" differs from the connecting element 2 of the first embodiment in that the lateral opening 6" for introducing the ball-shaped first rod end 4 is oriented in the opposite direction to the hook 22, and in that it also comprises, opposite to this first lateral opening 6", a narrower second lateral opening 26, broad enough to allow the passage of the shaft 25 of the first rod 3, but not enough for the ball-shaped first rod end 4.

This connecting element 2" can be used in essentially the same manner as the connecting element 2 of the first embodiment. In particular, the connecting element 2" can also be pre-assembled with the lock screw 7, as illustrated in FIGS. 9 and 10 for the first embodiment, and the ball-shaped first rod end 4 could also be introduced headfirst through the first lateral opening 6" into the socket 5, as illustrated in FIG. 11 for the first embodiment.

Figure 14:
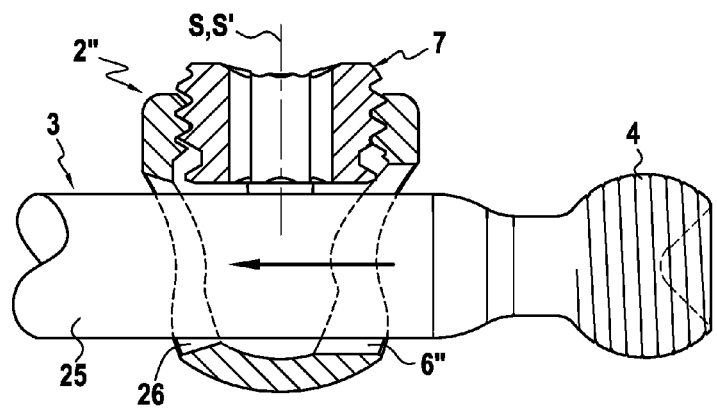
FIGS. 14 and 15 show how a ball-shaped rod end is introduced in the connecting element of FIG. 12, after the lock screw of FIG. 9, and locked therein.
Figure 15:
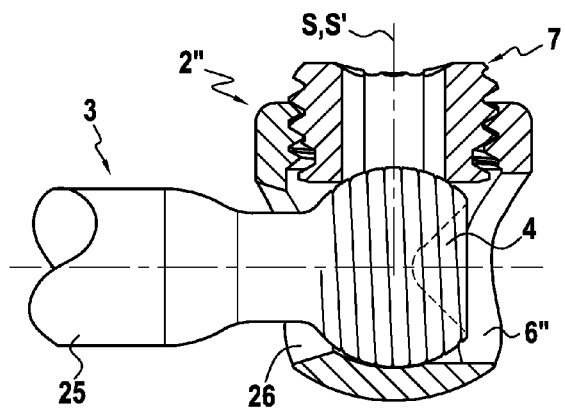

However, this second embodiment allows the insertion of the ball-shaped first rod end 4 through the first lateral opening 6" and into the socket 5 behind the second end 10 and the shaft 25, which re-exit the socket 5 through the second lateral opening 26. The first rod can thus be slid through the connecting element 2", as shown in FIG. 14, until the ball-shaped first rod end 4, not fitting through the second lateral opening 26, abuts against the partially-spherical inner surface defining the socket 5. As with the first embodiment, progressive tightening of the lock screw 7 against this ball-shaped first rod end 4 will then first hold the ball-shaped first rod end 4 into the socket 5 while still allowing angular adjustment of the ball-and-socket joint, and then rotationally lock this ball-and-socket joint, as shown in FIG. 15.

Those skilled in the art will recognize that the present invention may be manifested in a variety of forms other than the specific embodiments described and contemplated herein. Accordingly, departure in form and detail may be made without departing from the scope of the present invention as described in the appended claims.

The invention claimed is:

1. An orthopaedic device comprising:
    a connecting element suited for receiving at least part of a first rod and comprising:
        an anchor for securing said connecting element to a bone;
        a first lateral passage; and
        a top opening with a first inner screw thread; and
    a lock screw received within said top opening and rotatable about a rotational axis, the rotational axis intersecting the first lateral passage and comprising:
        a proximal face presenting a screw drive accessible from outside the connecting element;
        a distal end for locking said first rod within the connecting element, and
    wherein said lock screw is adapted to fit into said first lateral passage to be subsequently introduced into said top opening with the proximal face leading, and said distal end of the lock screw does not fit through said top opening, so as to enable pre-tensioning the lock screw within the connecting element, and
    wherein the proximal face of the lock screw is convexly rounded, cutting into the first inner screw thread at two opposite flattened sides of the lock screw.

2. The orthopaedic device according to claim 1, wherein said distal end of the lock screw presents a thread stop.

3. The orthopaedic device according to claim 1, wherein said top opening has a narrowed upper end.

4. The orthopaedic device according to claim 1, wherein said the distal lock screw is pre-tensioned within the connecting element.

5. The orthopaedic device according to claim 1, wherein said lock screw is suited to fit transversally through said first lateral passage while being substantially axially aligned with said top opening.

6. The orthopaedic device according to claim 1, wherein said connecting element further comprises a recess for receiving a second rod.

7. The orthopaedic device according to claim 6, wherein said connecting element further comprises a second inner screw thread for receiving a second lock screw for locking said second rod within said recess.

8. The orthopaedic device according to claim 1, wherein the bone comprises a vertebra.

9. An orthopaedic device comprising:
a first rod;
a second rod;
a connecting element comprising:
   an anchor for securing the connecting element to a bone;
   a first passage having a first lateral opening configured to receive the first rod therein;
   a top opening opening into the first passage, the top opening having an inner screw thread;
   a second passage configured to receive the second rod therein;
   a lock screw threadably engaged with the screw thread of the top opening to engage the first rod, the lock screw being rotatable about a rotational axis intersecting the first passage;
wherein said lock screw is adapted to fit through said first lateral opening to be subsequently introduced into said top opening with a proximal face of the lock screw leading, and a distal end of the lock screw does not fit through the top opening, so as to enable pre-tensioning the lock screw within the connecting element, and
wherein the connecting element is a monolithic structure including the anchor, the first passage, the first lateral opening, the top opening, and the second passage.

10. The orthopaedic device according to claim 9, wherein said connecting element further comprises a second inner screw thread for receiving a second lock screw for locking said second rod within said recess.

11. The orthopaedic device according to claim 9, wherein the top opening has a narrowed upper end.

12. The orthopaedic device according to claim 9, wherein the first lateral opening is a fully enclosed opening.

\* \* \* \* \*